United States Patent
Goetz et al.

(10) Patent No.: US 10,130,282 B2
(45) Date of Patent: Nov. 20, 2018

(54) VERIFICATION THAT A PATIENT WITH AN IMPLANTABLE MEDICAL SYSTEM CAN UNDERGO A MAGNETIC RESONANCE IMAGING SCAN

(75) Inventors: Steven M. Goetz, North Oaks, MN (US); Shahram Malekkhosravi, Maple Grove, MN (US); Todd V. Smith, Shoreview, MN (US); Kristin J. Malekkhosravi, Maple Grove, MN (US); Jeffrey R. Dixon, Andover, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 650 days.

(21) Appl. No.: 13/265,160

(22) PCT Filed: Apr. 28, 2010

(86) PCT No.: PCT/US2010/032661
§ 371 (c)(1),
(2), (4) Date: Oct. 19, 2011

(87) PCT Pub. No.: WO2010/126935
PCT Pub. Date: Nov. 4, 2010

(65) Prior Publication Data
US 2012/0035951 A1    Feb. 9, 2012

Related U.S. Application Data

(60) Provisional application No. 61/174,192, filed on Apr. 30, 2009.

(51) Int. Cl.
*G06Q 50/22*    (2018.01)
*A61B 5/055*    (2006.01)
(Continued)

(52) U.S. Cl.
CPC ............ *A61B 5/055* (2013.01); *A61B 5/0031* (2013.01); *A61N 1/37247* (2013.01);
(Continued)

(58) Field of Classification Search
None
See application file for complete search history.

(56) References Cited

U.S. PATENT DOCUMENTS 6,317,633 B1    11/2001  Jorgenson et al.
6,675,049 B2    1/2004   Thompson et al.
(Continued)

FOREIGN PATENT DOCUMENTS

WO    2007124273 A1    11/2007
WO    2010062988 A2    6/2010

OTHER PUBLICATIONS

PCT Application No. PCT/US2010/032661 International Search Report, dated Sep. 11, 2010.
(Continued)

*Primary Examiner* — Robert A Sorey
*Assistant Examiner* — Kristine K Rapillo
(74) *Attorney, Agent, or Firm* — Withers & Keys, LLC

(57) ABSTRACT

Verification that an implantable medical system within a patient is MRI safe is provided. Several verifications may be performed such as verifying that the device and leads are of an MRI safe type, that the leads have adequate electrical integrity, that the device has entered an MRI safe mode, that the lead routing and device placement are MRI safe, and that the MRI settings of the MRI machine are safe for the implantable medical system. The result of these verifications may lead to a conclusion that the implantable medical system of interest is or is not MRI safe for a given MRI scan. An indication of this result may be output such as via a display so that an MRI technician can have some assurance as to whether to conduct the MRI scan.

43 Claims, 15 Drawing Sheets

(51) Int. Cl.
  *A61B 5/00*    (2006.01)
  *A61N 1/372*   (2006.01)
  *G16H 40/63*   (2018.01)
  *G06F 19/00*   (2018.01)
  *A61N 1/37*    (2006.01)
  *A61N 1/08*    (2006.01)

(52) U.S. Cl.
  CPC ............. *G06F 19/00* (2013.01); *G06Q 50/22* (2013.01); *G16H 40/63* (2018.01); *A61B 2560/0271* (2013.01); *A61N 1/086* (2017.08); *A61N 1/3718* (2013.01)

(56) References Cited

U.S. PATENT DOCUMENTS

| | | | |
|---|---|---|---|
| 6,937,906 | B2 | 8/2005 | Terry et al. |
| 6,968,235 | B2 | 11/2005 | Belden et al. |
| 7,047,083 | B2 | 5/2006 | Gunderson et al. |
| 7,069,085 | B2 | 6/2006 | Cao et al. |
| 7,916,013 | B2 * | 3/2011 | Stevenson .......... A61N 1/37211 128/903 |
| 8,433,421 | B2 * | 4/2013 | Atalar et al. ............... 607/63 |
| 2003/0144705 | A1 | 7/2003 | Funke |
| 2004/0267233 | A1 | 12/2004 | Ginggen |
| 2005/0065570 | A1 | 3/2005 | Stein et al. |
| 2006/0167496 | A1 | 7/2006 | Nelson et al. |
| 2007/0021814 | A1 | 1/2007 | Inman et al. |
| 2008/0242944 | A1 | 10/2008 | Sharma |
| 2012/0130452 | A1 * | 5/2012 | Inman ................ A61N 1/36082 607/62 |
| 2012/0226140 | A1 * | 9/2012 | Min ..................... A61N 1/3718 600/411 |

OTHER PUBLICATIONS

PCT Application No. PCT/US2010/032661 International Preliminary Report on Patentability Chapter I, dated Nov. 11, 2011.

* cited by examiner

702

Neurostimulator
 Model No.   37712
 Serial No.  NFK*****

704

Date and Time

02 / 09 / 2009
14:21:47

Location                              MRI?      708

| Buttocks (Right)        ▽ |    ☐
| Buttocks (Right)           |
| Buttocks (Left)            |          706
| Abdomen (Right)            |
| Abdomen (Left)             |
| Axillary (Right)           |
| Axillary (Left)            |
| Flank (Right)              |
| Flank (Left)               |

Clear ⊺          (P)

NKF ****** 37712 John Doe

FIG. 8A

Lead Configuration
2x8

Lead Tip Location                    MRI?

I    Cervical spine ▽    ☐
II   Cervical spine ▽    ☐
III  Cervical spine ▽    ☐
IV   Cervical spine ▽    ☐
     Thoracic spine
     Lumbar spine
     Sacral nerve
     Torso SubQ PNS
     ONS
     Limb PNS
     Other Clear ⟲          Ⓟ

NKF ****** 37712 John Doe

FIG. 8B

Lead Model No.    MRI?

I   3777   ☐

II   3777   ☐

III   3777   ☐

IV   3777   ☐

— 716
— 720
— 718

Extensions

○ No    ○ 1    ⊙ 2

— 724

MRI?

I   3777   ☐

II   3777   ☐

— 726
— 722

ⓘ ─────────────

I: 0–7    II: 8–15

Clear ⌄    (P)

NKF ****** 37712 John Doe

FIG. 8C

Patient ID

John Doe

Patient Diagnosis

Failed Back Syndrome ▽

Physician Information

Jane Smith, M.D.

555-555-1212

Abandoned Leads or other AIMDs?
⦿ Yes
○ No

Notes

You are working with a virtual patient in demo mode. Patient has pain in the low back and throughout both legs and feet.

Clear τ     (P)

NKF ****** 37712 John Doe

FIG. 8D

VERIFICATION THAT A PATIENT WITH AN IMPLANTABLE MEDICAL SYSTEM CAN UNDERGO A MAGNETIC RESONANCE IMAGING SCAN

RELATED APPLICATIONS

This application is a U.S. National Stage filing under 35 U.S.C. 371 of PCT Application No. PCT/US2010/032661 filed Apr. 28, 2010, which claims priority to U.S. Provisional Application 61/174,192, filed on Apr. 30, 2009, the disclosures of each of the above which are incorporated by reference as if re-written herein in their entirety.

TECHNICAL FIELD

Embodiments are related to implantable medical systems. More particularly, embodiments are related to verifying that patients with implantable medical systems can undergo a magnetic resonance imaging scan.

BACKGROUND

Implantable medical systems including implantable medical devices (IMD) and associated implantable medical leads provide functions such as stimulation of muscle or neurological tissue and/or sensing of physiological occurrences within the body of a patient. Typically, the IMD is installed in a subcutaneous location that is accommodating and relatively accessible for implantation. For instance, to provide stimulation near the spine or pelvis, the IMD may be installed in a pocket located on the abdomen or upper buttocks region of the patient. The implantable medical lead is installed, either through a percutaneous procedure or a surgical procedure, depending upon the type of lead that is necessary.

Once installed, the lead extends from the stimulation site to the location of the IMD. The separation of the stimulation site to the location of the IMD varies, but may typically range from about 20 cm to about 100 cm. For relatively lengthy separation, if a lead of adequate length is unavailable then a lead extension may be implanted to span from the IMD to a proximal end of the implantable lead.

The implantable medical lead includes electrical connectors on a proximal end, electrodes on a distal end, and conductive filars interconnecting the connectors to the electrodes. When an extension is present, the implantable extension includes a connector block on the distal end that connects to the proximal connectors of the lead and includes connectors on the proximal end that connects to the IMD. The lead and the extension include a jacket, often made of a flexible but biocompatible polymer, and the filars are insulated from the body tissue by the jacket. However, the filars are not insulated by the jacket from the presence of electromagnetic radiation. Electromagnetic radiation in the radio frequency (RF) spectrum induces currents into the filars and thus presents current at the electrode that is unintended. In the patient's normal daily experience, the level of RF radiation that is encountered is at a negligible level, and there is no danger of heating of tissue by the unintended current that may result.

RF radiation poses a risk to tissue in contact with the electrodes when the intensity is significantly higher than the background levels. The surface area of each electrode is relatively small so that a small amount of tissue must dissipate a potentially large amount of induced current. In particular, if the patient is exposed to the RF radiation from a magnetic resonance imaging (MRI) scan, there is a high probability that tissue damage at the stimulation site(s) can occur. This tissue damage may be very dangerous, particularly so for neurological tissue. Therefore, patients with IMDs are typically not permitted to have a body coil MRI scan for at least these reasons.

Implantable medical systems are being developed to allow patients having such implantable medical systems to undergo an MRI scan. However, MRI technicians may be reluctant to conduct the MRI scan for a patient with an implantable medical system because the MRI technicians may not know whether the implantable medical system is safe for an MRI scan.

Embodiments provide a method of checking whether a magnetic resonance (MRI) image scan can be performed for a patient who has an implantable medical system. The method involves verifying by the external device that a route that the implantable medical lead takes within the patient is acceptable for an MRI scan. The method further involves providing by the external device an indication of whether the implantable medical system is acceptable for the MRI scan based on the verifying of the implantable medical lead.

SUMMARY

Embodiments address issues such as these and others by providing verification that an implantable medical system within a patient is safe for an MRI scan. An external device may conduct various checks to verify that the implantable medical system is or is not safe for a given MRI scan. The external device may then provide an indication of whether the implantable medical system is safe for the MRI scan so that the MRI technician may know whether the MRI scan can be conducted.

Embodiments provide a method of checking whether a magnetic resonance (MRI) image scan can be performed for a patient who has an implantable medical system. The method involves verifying by an external device that an implantable medical device of the implantable medical system is of a type that is acceptable for the MRI scan. The method further involves verifying by the external device that an implantable medical lead of the implantable medical system is of a type that is acceptable for the MRI scan. The method also further involves providing by the external device an indication of whether the implantable medical system is acceptable for the MRI scan based on the verifying of the implantable medical device and the implantable medical lead.

Embodiments provide a method of checking whether a magnetic resonance (MRI) image scan can be performed for a patient who has an implantable medical system. The method involves verifying by the external device that the implantable medical device has entered an MRI safe state. The method further involves providing by the external device an indication of whether the implantable medical system is acceptable for the MRI scan based on the verifying of the implantable medical device.

Embodiments provide a method of checking whether a magnetic resonance (MRI) image scan can be performed for a patient who has an implantable medical system. The method involves verifying by the external device that the implantable medical lead has adequate integrity by lacking short circuits and open circuits. The method further involves providing by the external device an indication of whether the implantable medical system is acceptable for the MRI scan based on the verifying of the implantable medical lead.

Embodiments provide a method of checking whether a magnetic resonance (MRI) image scan can be performed for a patient who has an implantable medical system. The method involves analyzing by the external device MRI scan settings of an MRI machine. The method further involves providing by the external device an indication of whether the implantable medical system is acceptable for the MRI scan based on the analyzing of the MRI scan settings.

Embodiments provide a method of checking whether a magnetic resonance (MRI) image scan can be performed for a patient who has an implantable medical system. The method involves verifying by the external device that a route that the implantable medical lead takes within the patient is acceptable for an MRI scan. The method further involves providing by the external device an indication of whether the implantable medical system is acceptable for the MRI scan based on the verifying of the implantable medical lead.

Embodiments provide a method of checking whether a magnetic resonance (MRI) image scan can be performed for a patient who has an implantable medical system. The method involves verifying by the external device that a placement of the implantable medical device within the patient is acceptable for an MRI scan. The method further involves providing by the external device an indication of whether the implantable medical system is acceptable for the MRI scan based on the verifying of the implantable medical device.

Embodiments provide an external device for checking whether a magnetic resonance (MRI) image scan can be performed for a patient who has an implantable medical system. The external device includes a processor configured to verify that an implantable medical device of the implantable medical system is of a type that is acceptable for the MRI scan. The processor is further configured to verify that an implantable medical lead of the implantable medical system is of a type that is acceptable for the MRI scan. The processor is further configured to provide an indication of whether the implantable medical system is acceptable for the MRI scan based on the verifying of the implantable medical device and the implantable medical lead.

Embodiments provide an external device for checking whether a magnetic resonance (MRI) image scan can be performed for a patient who has an implantable medical system. The external device includes a processor configured to verify that an implantable medical device of the implantable medical system has entered an MRI safe state. The processor is further configured to provide an indication of whether the implantable medical system is acceptable for the MRI scan based on the verifying of the implantable medical device.

Embodiments provide an external device for checking whether a magnetic resonance (MRI) image scan can be performed for a patient who has an implantable medical system. The external device includes a processor configured to verify that an implantable medical lead of the implantable medical system has adequate integrity by lacking short circuits and open circuits. The processor is further configured to provide an indication of whether the implantable medical system is acceptable for the MRI scan based on the verifying of the implantable medical lead.

Embodiments provide an external device for checking whether a magnetic resonance (MRI) image scan can be performed for a patient who has an implantable medical system. The external device includes a processor configured to analyze MRI scan settings of an MRI machine. The processor is further configured to provide an indication of whether the implantable medical system is acceptable for the MRI scan based on the analyzing of the MRI scan settings.

Embodiments provide an external device for checking whether a magnetic resonance (MRI) image scan can be performed for a patient who has an implantable medical system. The external device includes a processor configured to verify that a route that an implantable medical lead of the implantable medical system takes within the patient is acceptable for an MRI scan. The processor is further configured to provide an indication of whether the implantable medical system is acceptable for the MRI scan based on the verifying of the implantable medical lead.

Embodiments provide an external device for checking whether a magnetic resonance (MRI) image scan can be performed for a patient who has an implantable medical system. The external device includes a processor configured to verify that a placement of an implantable medical device of the implantable medical system within the patient is acceptable for an MRI scan. The processor is further configured to provide an indication of whether the implantable medical system is acceptable for the MRI scan based on the verifying of the implantable medical device.

DESCRIPTION OF THE DRAWINGS

FIGS. 8A-8F show screenshots of an external device embodiment that allows entry of information about an implantable medical system that is related to verification of MRI safety.

DETAILED DESCRIPTION

Embodiments provide for verification of whether an implantable medical system within a patient is MRI safe such that the patient may undergo an MRI scan. The verification may be performed by an external device that communicates with the implantable medical device (IMD) of the patient to gather MRI related information. The verification may further involve instructing the IMD to enter an MRI safe mode, specifying and/or measuring MRI machine settings, and providing an indication of whether the implantable medical system is safe for a given MRI scan.

Figure 1:
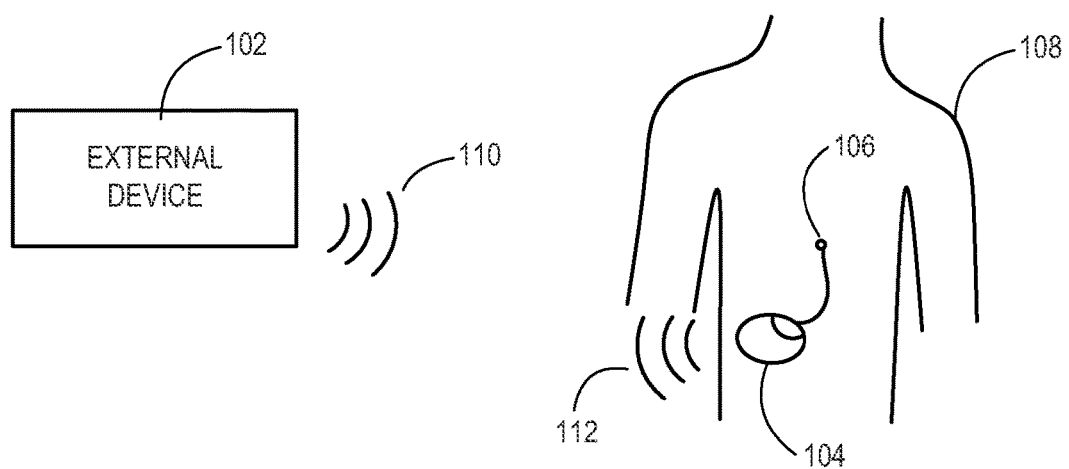
FIGS. 1 and 2 show an operating environment for illustrative embodiments that verify that an implantable medical system is safe for an MRI scan.

FIG. 1 shows an external device 102 in communication with an IMD 104 that is implanted within a patient 108. The external device 102 may be one of various device types, such as a device programmer, a patient therapy manager (PTM), or a dedicated MRI verification device. Likewise, the IMD 104 may be of various device types as well such as a stimulator or a monitoring device. The IMD 104 has medical components such as implantable medical leads 106 that may be used for stimulation and/or sensing. The IMD 104 together with the leads 106 forms an implantable medical system.

The external device 102 and the IMD 104 typically communicate through a form of telemetry. In the case of a wireless communication link, wireless signals 110 are sent by the external device 102 and are received by the IMD 104. Likewise, wireless signals 112 are sent by the IMD 104 and are received by the external device 102. As an example, the telemetry may use radio frequency (RF) signaling where an antenna of the external device 102 and the IMD 104 are separated by a larger distance than occurs with near field telemetry to provide added convenience. Near field telemetry may be used instead of RF signaling.

Typically, when the time for verifying that the implantable medical system is MRI safe, the external device 102 initiates a communication session with the IMD 104. The external device 102 may query the IMD 104 for various pieces of information relating to the IMD 104 and the leads 106 that the IMD 104 maintains. The external device 102 makes a determination about whether the implantable medical system is MRI safe by analyzing this information.

Figure 2:
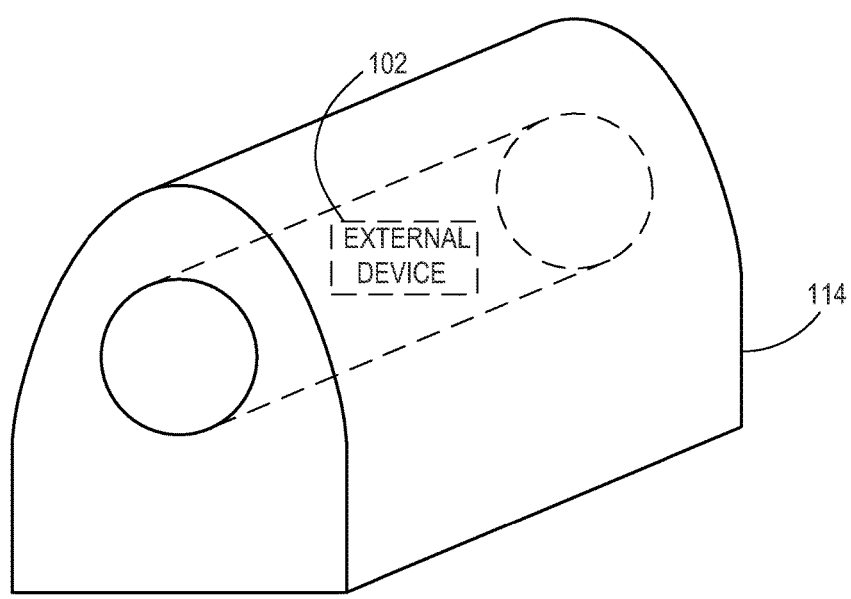

FIG. 2 shows the remaining portion of the operating environment for the various embodiments. Here, an MRI machine 114 is shown. As is well known, the MRI machine 114 produces various static and gradient magnetic fields as well as radio frequency radiation. Settings of the MRI machine 114 control aspects of these fields and radiation, such as the intensities of each.

A given implantable medical system may be MRI safe for a particular range of these settings. Therefore, one aspect of verifying whether the implantable medical system is MRI safe for a given MRI scan is to directly measure these values by placing the external device 102 within the patient cylinder of the MRI machine 114. In such a case, the external device 102 includes MRI related sensors to measure these values directly and to base a conclusion of whether the implantable medical system is MRI safe in part on these measured values.

Figure 3:
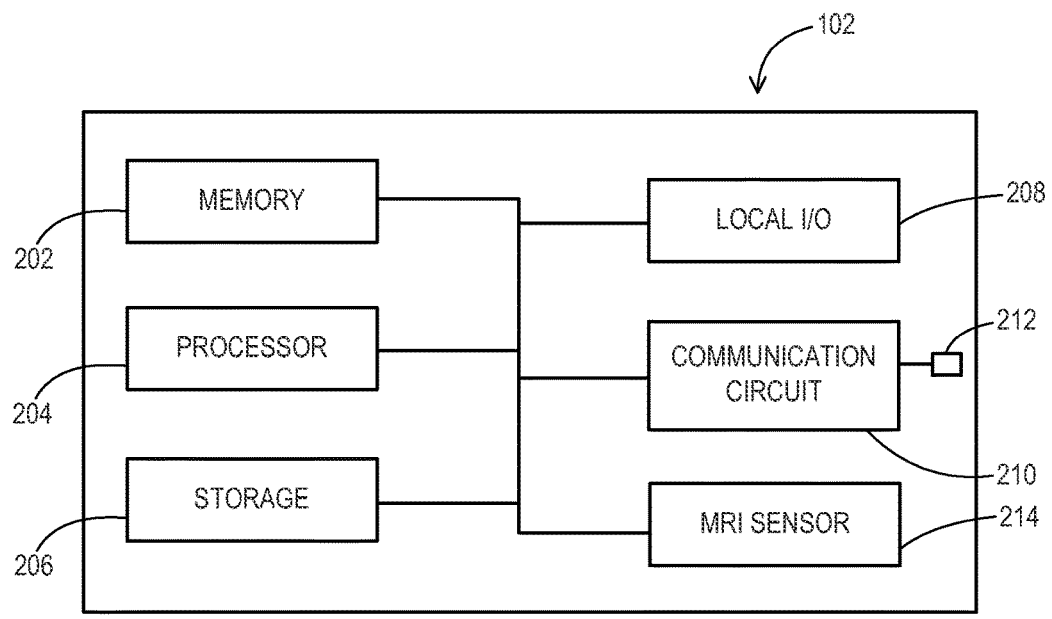
FIG. 3 shows an illustrative external device embodiment that communicates with an implantable medical device (IMD) to verify that the implantable medical system is safe for an MRI scan.

FIG. 3 shows components of one example of the external device 102. The external device 102 includes a memory 202, a processor 204, and may also include a storage device 206. The external device 102 may also include local input/output (I/O) ports 208 such as to provide local screen displays and to receive user input via a keypad, touchscreen, and so forth. The external device 102 also includes communication circuitry 210 used to establish the telemetry to the IMD 104. The communication circuitry 210 may drive a signal propagation tool 212, such as an RF antenna or a read/write head.

The memory 202 may be used to store information in use by the processor 204. For instance, the memory 202 may store the MRI related information that has been obtained from the IMD 104 as well as any information related to the MRI machine 114 such as the settings and/or measured values. The memory 202 may also store programming that is used by the processor 204 to control the verification actions of the external device 102. The memory 202 may be of various types, such as volatile, non-volatile, or a combination of the two.

The storage device 206 may be used to store information for a long term and may be of various types such as non-volatile so that the information is retained when the external device 102 is powered off. The storage device 206 may also store programming for the processor 204 that is implemented to control the verification actions. Examples of the storage device 206 include electronic, magnetic, and optical drives. However, storage other than the magnetic type may be used where the external device 102 may be measuring MRI values directly. The storage device 206 and the memory 202 are both examples of computer readable media that may store information in the form of computer programming, data structures, and the like.

The processor 204 performs logical operations such as those of FIGS. 6A-6D to allow MRI related information to be gathered from the IMD 104 and the MRI machine 114. The processor 204 may perform additional logical operations to provide an output of information such as a visual display of allowable MRI settings and an indication of whether the implantable medical system is MRI safe. The processor 204 may be of various forms. For instance, the processor 204 may be a general-purpose programmable processor that executes software that is stored on the storage device 206 or elsewhere. Other examples include a dedicated purpose hardware circuit or hard-wired digital logic. The processor 204 may communicate with the various other components through one or more data buses.

The external device 102 may also include MRI sensors 214. These sensors 214 may be used to measure the MRI values for static and gradient magnetic fields and for RF power during a test prior to placing the patient within the MRI machine 114. The MRI sensors 214 may include Hall effect sensors, coils to detect induced currents, antennas to receive RF energy and to measure its power via root mean square calculations or other means, phased locked loops or other circuitry to measure the frequency of received RF or magnetic energy, or a load material with coupled temperature sensing such as a thermocouple or thermistor to measure induced heating.

Figure 4:
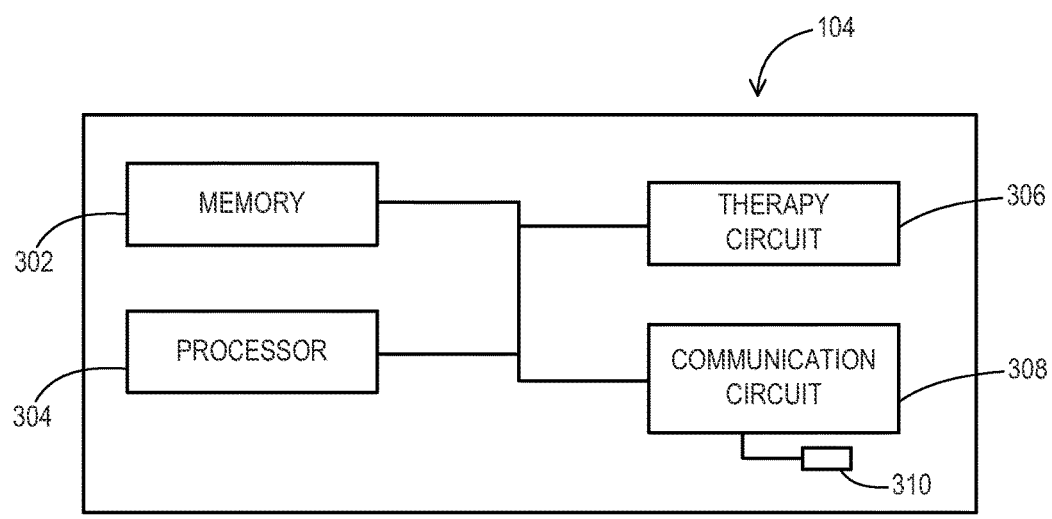
FIG. 4 shows an illustrative IMD embodiment that communicates with an external device to verify that the implantable medical system is safe for an MRI scan.

FIG. 4 shows components of one example of the IMD 104. The IMD 104 includes a memory 302 and a processor 304. The IMD 104 also includes therapy circuitry 306 that performs a medical task such as stimulation and/or monitoring. The IMD 104 also includes communication circuitry 308 used to establish the telemetry to the external device 102. The communication circuitry 308 may drive a signal propagation tool 310, such as an integral RF or near field antenna.

The memory 302 may be used to store information in use by the processor 304 such as programming and data values including the MRI related information. The memory 302 may store additional information including therapy parameters that are used to control the therapy circuitry 306. The memory 302 may be of various types such as volatile, non-volatile, or a combination of the two. The memory 302 is also an example of computer readable media that may store information in the form of computer programming, data structures, and the like.

The processor 304 performs logical operations to allow communication sessions with the external device 102 to occur. These logical operations may involve responding to a query by the external device 102 for the MRI related information. The processor 304 may also perform other operations requested by the external device 102, such as to do impedance testing to check for impedances that are outside of a range acceptable for MRI safety, such as where short circuits or open circuits of the individual filar/electrode combinations are present. The processor 304 may be of various forms like those discussed above for the processor 204 of the external device 102. The processor 304 may communicate with the various other components through one or more data buses.

Figure 5:
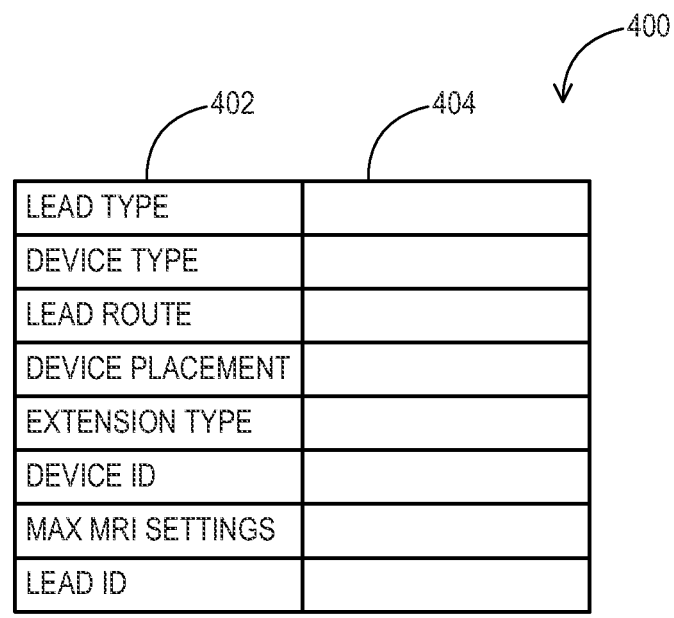
FIG. 5 shows an example of a table that may be stored in memory of the IMD embodiment.
Figure 6A:
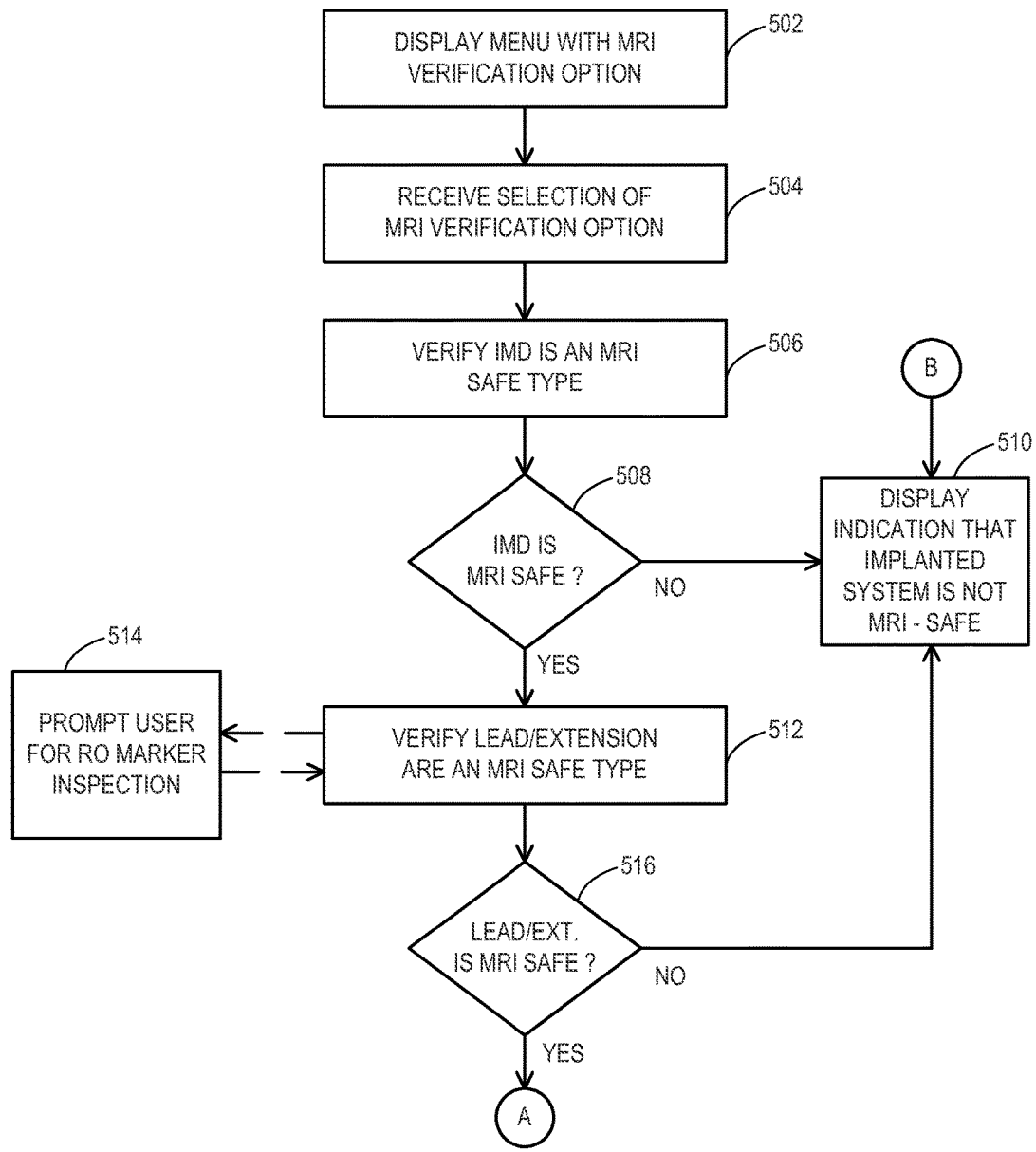
FIGS. 6A-6D show an example of operational flow of external device embodiments that verify that an implantable medical system is safe for an MRI scan.
Figure 6B:
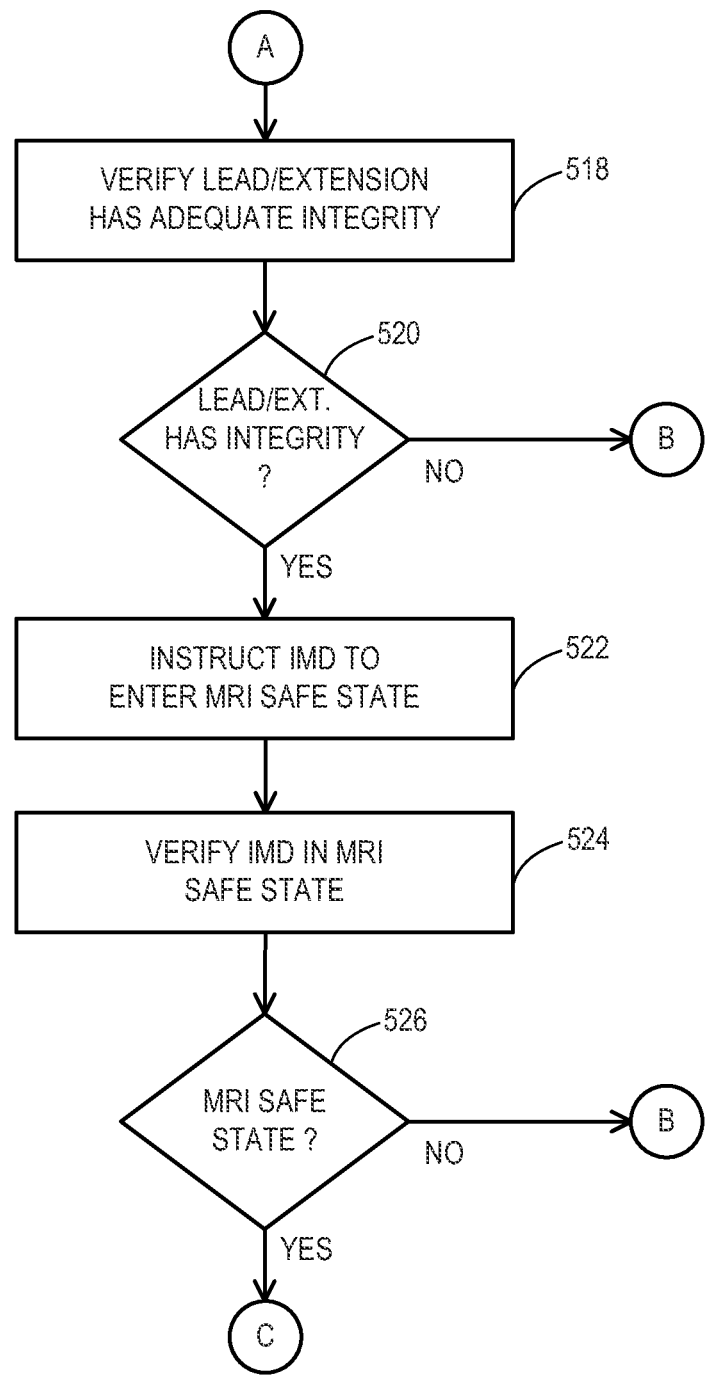
Figure 6C:
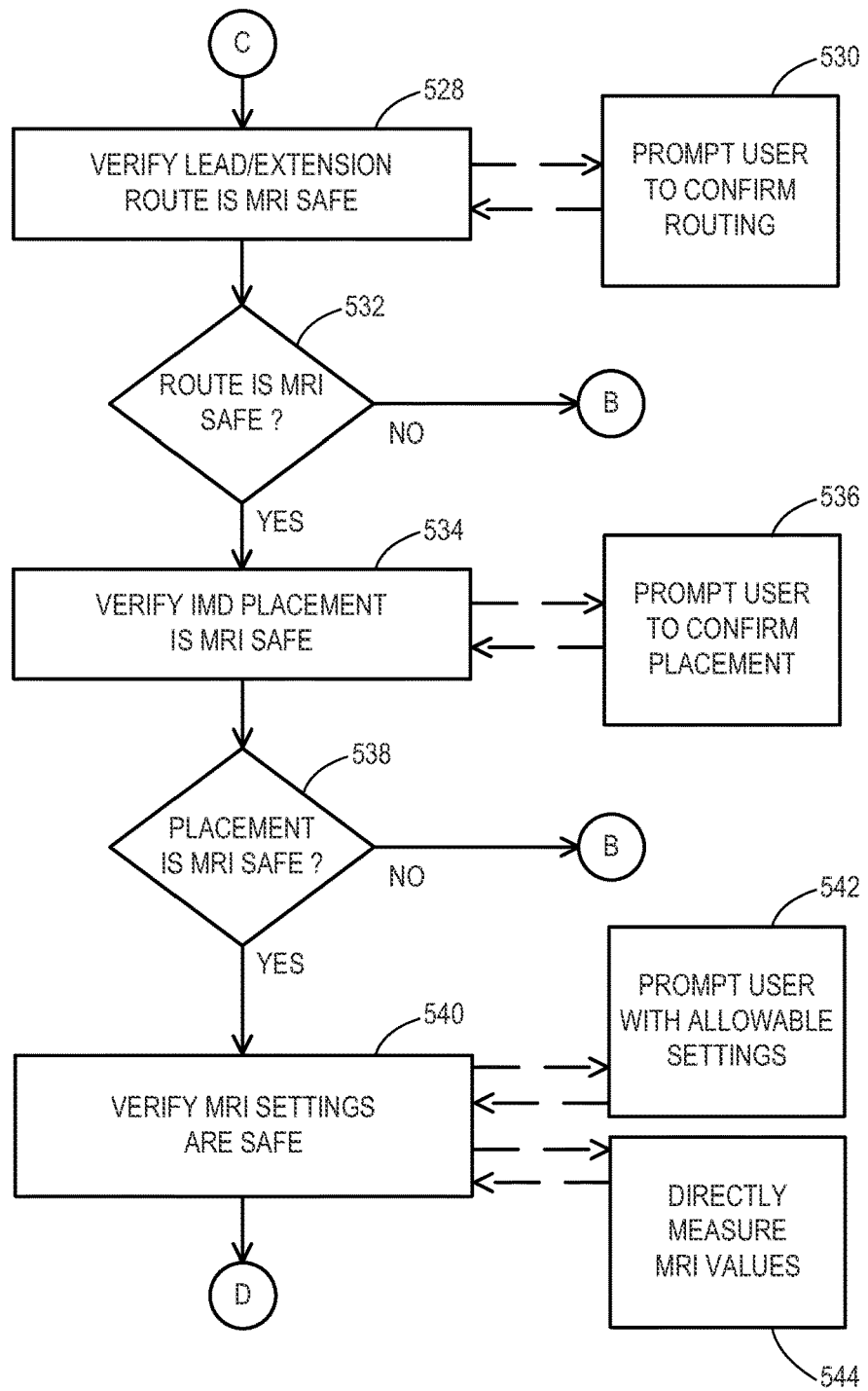
Figure 6D:
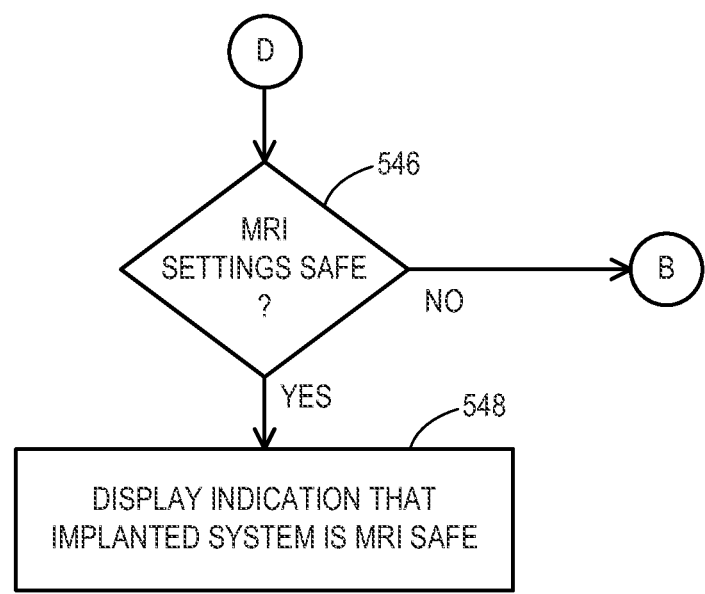

FIG. 5 shows an example of a data structure 400 that may be maintained in the memory 302 of the IMD 104. This data structure 400 includes the MRI related information that the external device 102 may request. Column 402 specifies that information that is stored in each entry of a column 404. The name in column 402 may be a standard convention shared among the external device 102 and the IMD 104 such that if the external device 102 requests information by name, the IMD 104 can find and return the information. Alternatively, the IMD 104 and external device 102 may share a standard convention for the storage location of particular pieces of MRI related data such that the external device 102 may request information located at a particular memory location and the IMD 104 may then access that location and return the information stored there.

FIG. 5 shows some of the types of MRI information that may be requested. This MRI related information may be placed into the memory 302 at the time of implant or at some subsequent time by a clinician using a device programmer. Entry of such information is discussed in further detail below with reference to the screenshots of FIGS. 8A-8D. Other MRI related information may also be included in the memory 302, such as whether abandoned leads or devices are present within the patient having the IMD 104 being queried.

Figure 7A:
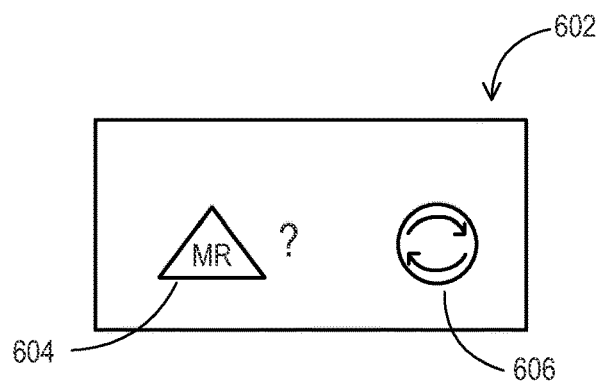
FIGS. 7A-7C show screenshots of an external device embodiment that verifies whether the implantable medical system is safe for an MRI scan and shows a verification result.

FIG. 6A-6D shows one example of logical operations that may be performed by the external device 102 when attempting to verify whether an implantable medical system is safe for a given MRI scan. The logical operations begin by displaying a menu with an MRI verification option at a display operation 502. FIG. 7A provides one example of a display 602 that the external device 102 may provide. An MRI safe verification logo 604 may be included to indicate that the verification is an option. An activation control 606 may be presented to allow a user to select the control 606 and initiate the verification process.

The selection of the control 606 is received at a selection operation 504. The external device 102 then begins the verification process. At a first verification operation 506, the external device 102 verifies that the IMD 104 is an MRI safe type. This verification may occur by querying the IMD 104 for the device type if available, for a device ID such as a model and/or serial number if available, and/or for MRI allowable settings that may reveal the device type. The external device 102 determines from this information whether the IMD 104 is a type that is MRI safe at a query operation 508. Here, the external device 102 may compare the information received from the IMD 104 to a table relating such information to an indicator of whether the IMD 104 is a type that is MRI safe.

If the external device 102 finds that the IMD 104 is not a type that is MRI safe, then the external device 102 generates a display at a display operation 510. An example of this display is shown as the display 614 of FIG. 7C. The display 614 indicates to the user that the implantable medical system is not safe and that the MRI scan should not be conducted. A logo 616 provides the indication that the implantable medical system is not MRI safe. The display 614 may provide additional information as well, such as an error code 618 that is related to the reason that the implantable medical system is not MRI safe. An identifier 620 of the IMD 104 may also be displayed along with the date and time. This information may be stored to logs so that a clinician can later review this information and determine if a corrective action is possible.

If the external device 102 finds at the query operation 508 that the IMD 104 is an MRI safe type, then the external device 102 proceeds with the verification process. The external device 102 verifies whether the lead and extension, if any, are an MRI safe type at a second verification operation 512. This verification may occur by querying the IMD 104 for the lead and extension type if available or for an ID such as a model and/or serial number if available.

In addition to or as an alternative to querying the IMD 104 for the lead/extension 106 information, the external device 102 may prompt the user to inspect the lead/extension 106 using X-ray or fluoroscopy at an inspection operation 514. The user will look for a radiopaque (RO) marker attached to the lead/extension 106 where the RO marker may provide an indicator that the lead/extension 106 is MRI safe. The user may enter a yes or no into the external device 102 in response to the prompting to indicate whether the RO marker is present that identifies the lead/extension as being MRI safe.

The external device 102 determines from this information whether the lead/extension 106 is MRI safe at a query operation 516. Here, the external device 102 may compare the information received from the IMD 104 to a table relating such information to an indicator of whether the lead/extension 106 is MRI safe. Additionally or alternatively, the external device 102 may conclude that the lead/extension 106 is or is not MRI safe based on the user entry regarding the presence of the RO marker.

If the external device 102 finds that the lead/extension 106 is not MRI safe through either or both techniques, then the external device 102 generates the display of the indication at the display operation 510. The display may be that of FIG. 7C which is discussed above.

If the external device 102 finds at the query operation 516 that the lead/extension 106 is an MRI safe type, then the external device 102 proceeds with the verification process. The external device 102 verifies whether the lead and extension, if any, have adequate electrical integrity at a third verification operation 518. This verification may occur by the external device 102 requesting that the IMD 104 perform a set of simple and/or complex impedance tests on the lead/extension 106 and querying the IMD 104 for results of the impedance testing. The impedance testing detects whether there are circuits producing overly low impedance such as short circuits or circuits producing overly high impedance such as open circuits along the lead/extension 106 that should not be there.

At a query operation 520, the external device 520 determines from the lead/extension impedance testing results whether the lead/extension 106 has adequate integrity for an MRI scan. If impedance measurements fall outside of acceptable ranges, for example because short circuits and/or open circuits are present where they should not be, then the display operation 510 provides the display 614 that the implantable medical system is not MRI safe.

If the lead/extension integrity is adequate, then the verification process proceeds. The next operation may be for the external device 102 to instruct the IMD 104 to enter an MRI safe state in preparation for the MRI scan at an instruction operation 522. The MRI safe state may be to turn off stimulation, to reconfigure circuitry, and so forth.

The external device 102 may then perform a fourth verification operation 524 where the external device 102 queries the IMD 104 for its current state to ensure that the MRI safe state has been achieved. Query operation 526 detects whether a response form the IMD 104 indicates that the MRI safe mode is active. If not, then the indication that the implantable medical system is not MRI safe is provided at the display operation 510. The fourth verification operation 524 may perform additional checks of the IMD state that may also be pertinent to MRI safety including checking that the IMD 104 is operating normally and/or that a power source of the IMD 104 is at an acceptable level.

Where the MRI safe mode is achieved at the IMD 104, then the verification process continues. A fifth verification operation 528 verifies whether the lead/extension route and tip placement within the patient is MRI safe. This verification may occur by querying the IMD 104 for the lead and extension route and tip placement if available. The tip placement may be inferred from the routing but if the tip placement is available, then it may be reviewed to determine that the tip placement is MRI safe.

In addition to or as an alternative to querying the IMD 104 for the lead/extension route and tip placement, the external device 102 may prompt the user to inspect the lead/extension 106 route using X-ray or fluoroscopy at a confirmation operation 530. The user may have observed this lead/extension routing when attempting to find the RO marker previously discussed. The user may enter an indication into the external device 102 in response to the prompting to indicate routing.

The external device 102 determines from this information whether the lead/extension route and resulting tip placement is MRI safe at a query operation 532. Here, the external device 102 may compare the information received from the IMD 104 to a table relating such information to an indicator of whether the lead/extension route and resulting tip placement is MRI safe.

If the external device 102 finds that the lead/extension route and resulting tip placement is not MRI safe through either or both techniques, then the external device 102 generates the display of the indication at the display operation 510. The display may be that of FIG. 7C which is discussed above.

If the external device 102 finds at the query operation 532 that the lead/extension route and resulting tip placement is MRI safe, then the verification process continues. The external device 102 performs a sixth verification operation 534 to verify that the placement of the IMD 104 is MRI safe. This verification may occur by querying the IMD 104 for the placement if available.

In addition to or as an alternative to querying the IMD 104 for the placement, the external device 102 may prompt the user to inspect the placement using X-ray or fluoroscopy at a confirmation operation 536. The user may have observed this placement when attempting to find the RO marker previously discussed. The user may enter an indication into the external device 102 in response to the prompting to indicate the placement.

The external device 102 determines from this information whether the IMD placement is MRI safe at a query operation 538. Here, the external device 102 may compare the information received from the IMD 104 to a table relating such information to an indicator of whether the IMD placement is MRI safe.

If the external device 102 finds that the IMD placement is not MRI safe through either or both techniques, then the external device 102 generates the display of the indication at the display operation 510. The display may be that of FIG. 7C which is discussed above.

If the external device 102 finds at the query operation 538 that the device placement is MRI safe, then the verification process continues. The external device 102 performs a seventh verification operation 540 to verify that MRIs settings of the MRI machine 114 are safe for the implantable medical system. One manner of verifying these MRI settings is to prompt the user to review a display of the allowable settings for the current implantable medical system at a settings operation 542. These settings may be stored in the external device 102 in advance or may be stored in the IMD 104 and requested by the external device 102 during the settings operation 542. The user may be prompted to confirm that the allowable settings have been configured on the MRI machine 114.

Additionally or alternatively, the external device 102 may include MRI related sensors 214. The external device 102 may prompt the user to place the external device 102 into the MRI machine 114 and activate the MRI scan using MRI settings intended for the MRI scan of the patient. The external device 102 then directly measures the MRI values for static and gradient fields and for RF power at a measurement operation 544.

The external device 102 determines from this measured information whether the MRI settings are safe at a query operation 546. Here, the external device 102 may rely on the input by the user and/or may compare the measured values to a table of the allowable settings.

If the external device 102 finds that the MRI settings are not within the allowable range to be safe for the implantable medical system of interest, then the external device 102 generates the display of the indication at the display operation 510. The display may be that of FIG. 7C which is discussed above. If the external device 102 finds at the query operation 546 that the MRI settings are within the allowable range to be safe for the implantable medical system of interest, then the verification process concludes by displaying an indicator that the implantable medical system is MRI safe for this MRI scan at a display operation 548.

Figure 7B:
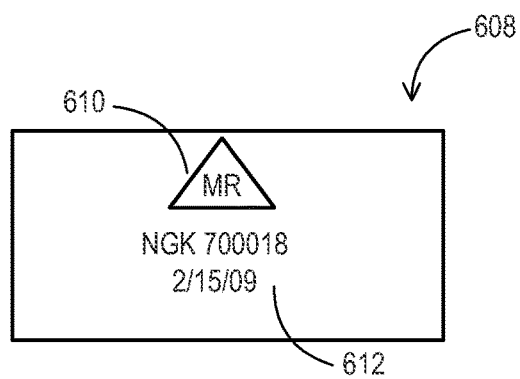
Figure 7C:
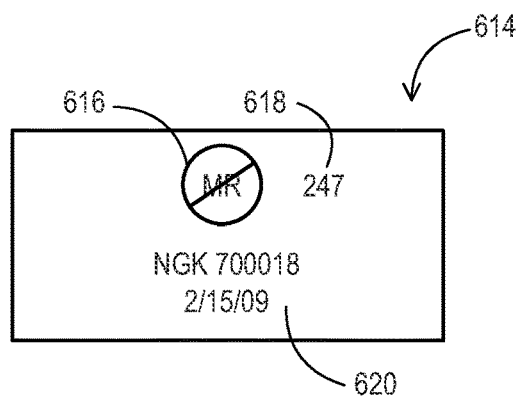

An example of this display for an MRI safe implantable medical system is shown as the display 608 of FIG. 7B. The display 608 indicates to the user that the implantable medical system is safe and that the MRI scan can be conducted. A logo 610 provides the indication that the implantable medical system is MRI safe. The display 608 may provide additional information as well such as an identifier 612 of the IMD 104 along with the date and time. Furthermore, the display may provide other information such as a number that indicates the level of MRI scan that the implantable medical system is deemed safe to undergo.

This information including the date, time, activation of the MRI safe state, level of MRI scan that is safe, and the verification results may be stored to logs in the external device 102 and/or within the IMD 104 so that a clinician can later review this information should there be a need to do so. For instance, reviewing logs that indicate that the MRI safe state was activated, or even that an MRI scan occurred, may allow a clinician to better interpret device diagnostics.

The logical operations of FIGS. 6A-6D are shown as one example. Other examples are possible. In particular, a different number of verifications could be performed. Furthermore, the verifications could be performed in a different sequence. However, the sequence shown in FIGS. 6A-6D is considered an efficient manner of verifying the MRI safety because the majority of the user interaction is later in the sequence so that if an early verification fails, the user interaction may not be needed in order to draw the conclusion that the implantable medical system is not MRI safe.

Figure 8E:

FIGS. 8A-8F show various illustrative screenshots of an external device, such as the external device 102 or an entirely different external device such as a clinician programmer that is present at the time of implantation and not present at the subsequent MRI scan. FIG. 8A shows a screenshot 702 that provides a user with the ability to specify the placement of the IMD 104. The IMD 104 has a model and serial number shown in area 704 that has been obtained by the external device. A drop down menu 706 allows the user to select the particular location where the IMD 104 is placed. This information may be written to the memory 302 of the IMD 104 so that it can be obtained by the external device 102 from the IMD 104 during the MRI safe verification process.

In some embodiments, the external device providing the screenshot 702 may have a built-in table to conclude whether a given IMD 104 placement is MRI safe. In other embodiments, the screenshot 702 may provide a checkbox 708 to allow the user to select whether the placement is MRI safe. In other embodiments, the external device providing the screenshot 702 may not be the external device 102 present at the MRI scan and may rely on the external device 102 present at the MRI scan to decide whether the placement is MRI safe.

FIG. 8B shows a screenshot 710 that provides a user with the ability to specify the lead tip location. A drop down menu 712 allows the user to select the particular location where the tip of each lead 108 is placed. This information may be written to the memory 302 of the IMD 104 so that it can be obtained by the external device 102 from the IMD 104 during the MRI safe verification process.

In some embodiments, the external device providing the screenshot 710 may have a built-in table to conclude whether a given lead tip placement is MRI safe. In other embodiments, the screenshot 710 may provide a checkbox 714 for each tip to allow the user to select whether the placement of each is MRI safe. In other embodiments, the external device providing the screenshot 710 may not be the external device 102 at the MRI scan and may rely on the external device 102 at the MRI scan to decide whether the lead tip placements are MRI safe.

FIG. 8C shows a screenshot 716 that provides a user with the ability to specify the lead model, number of extensions, and extension model. A data field 718 for each lead 106 allows the user to select the particular model of each. A data field 722 for each extension allows the user to select the particular model of each. A set of bubble entries 724 may allow the user to select the number of extensions that are in use. This information may be written to the memory 302 of the IMD 104 so that it can be obtained by the external device 102 from the IMD 104 during the MRI safe verification process.

In some embodiments, the external device providing the screenshot 716 may have a built-in table to conclude whether a given lead model, extension model, and number of extensions is MRI safe. In other embodiments, the screenshot 716 may provide checkboxes 720,726 for each lead and extension to allow the user to select whether the each lead 106 and extension is MRI safe. In other embodiments, the external device providing the screenshot 716 may not be the external device 102 at the MRI scan and may rely on the external device 102 at the MRI scan to decide whether the lead model, extension model, and number of extensions are MRI safe.

FIG. 8D shows a screenshot 728 that provides a user with the ability to specify patient and doctor information but to also specify whether the patient has abandoned leads or devices within the body of the patient via a pair of yes/no bubble entries 730. If abandoned leads or devices are present, then the external device 102 may conclude from that alone that it is not safe to conduct an MRI scan, or the external device 102 may prompt the user to attempt to establish communications with an abandoned device to conduct a verification process for the abandoned device as well, and use the combination of the results to determine if conducting the MRI scan is safe.

FIG. 8E shows a screenshot 732 that provides a user with the ability to select reports to create and print or otherwise output based on information gathered by the external device through communication sessions with the IMD 104 and through user interaction. A series of checkboxes are provided to allow the reports to be selected for creation and output. In particular, a pair of checkboxes 734 allow for MRI related data to be included in the report, such as the data specified in FIGS. 8A-8D and also the data for the successful or failed attempts to verify from FIGS. 7B and 7C.

Figure 8F:
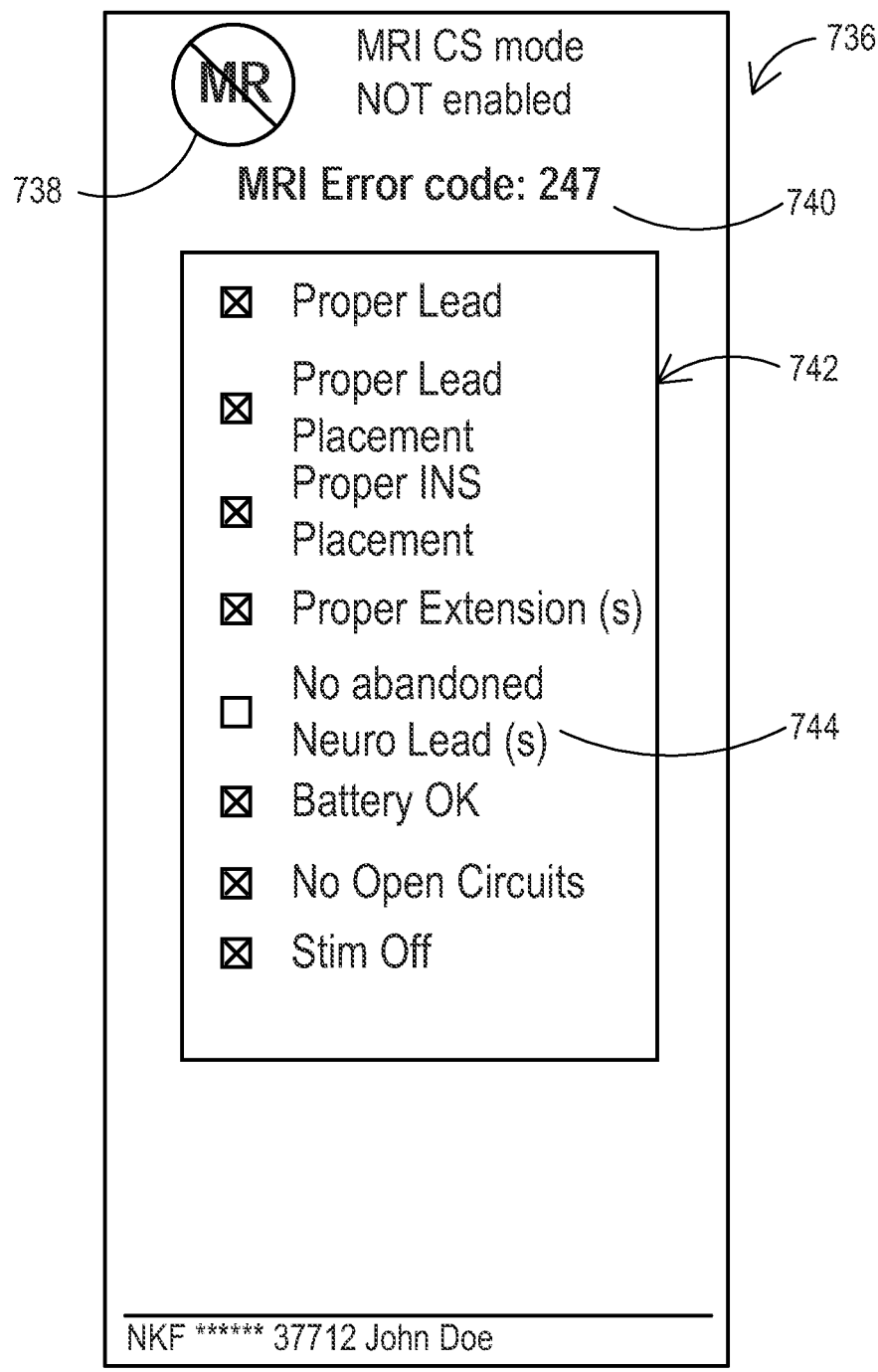

FIG. 8F shows a screenshot 736 that indicates that the implantable medical system of interest is not MRI safe. A logo 738 indicates the lack of MRI safety. An error code of area 740 provides an indication of why the verification of MRI safety has failed. An area 742 provides a collection of checkboxes that provide a particular reason that is related to the error code. In this example, the checkbox 744 is unchecked, indicating that an abandoned lead is present. As shown in FIG. 8D, the user has specified that an abandoned lead is present and thus the lack of MRI safety is driven by that user input in this example.

A similar display could be provided to show that the implantable medical system is MRI safe. In such an example, the MRI safe logo is displayed and all checkboxes of area 742 are checked.

While embodiments have been particularly shown and described, it will be understood by those skilled in the art that various other changes in the form and details may be made therein without departing from the spirit and scope of the invention.

What is claimed is:

1. A method of checking whether a magnetic resonance (MRI) image scan can be performed for a patient who has an implantable medical system, the method comprising:
   establishing by an external device a telemetry communication session with the implantable medical system;
   verifying by the external device that an implantable medical device of the implantable medical system is of a type that is acceptable for the MRI scan by sending a query to the implantable medical device via the telemetry communication session;
   verifying by the external device that an implantable medical lead of the implantable medical system is of a type that is acceptable for the MRI scan;
   providing by the external device an indication of whether the implantable medical system is acceptable for the MRI scan based on the verifying of the implantable medical device and the implantable medical lead;
   analyzing by the external device MRI scan settings of an MRI machine by the external device taking measurements within the MM machine during an MRI scan by the MRI machine; and
   providing by the external device an indication of whether the implantable medical system is acceptable for the MRI scan based on the analyzing of the MRI scan settings.

2. The method of claim 1, wherein verifying by the external device that the implantable medical device is of a type that is acceptable for the MRI scan comprises:
   receiving at the external device a response to the query that includes information related to the type of the implantable medical device; and analyzing the received information to determine whether the implantable medical device is of the type that is acceptable for the MRI scan.

3. The method of claim 2, wherein the received information comprises MRI scan related settings.

4. The method of claim 2, wherein the received information comprises an identification of the implantable medical device.

5. The method of claim 1, wherein verifying by the external device that the implantable medical lead is of a type that is acceptable for the MRI scan comprises:
sending a query from the external device to the implantable medical device;
receiving at the external device a response to the query that includes information related to the type of the implantable medical lead; and
analyzing the received information related to the type of the implantable medical lead to determine whether the implantable medical lead is of the type that is acceptable for the MRI scan.

6. The method of claim 5, wherein the received information related to the type of the implantable medical lead comprises an identification of the implantable medical lead.

7. The method of claim 1, further comprising sending by the external device a command for the implantable medical device to enter an MRI safe state.

8. The method of claim 1, further comprising verifying by the external device that the implantable medical device has entered an MRI safe state.

9. The method of claim 1, further comprising verifying by the external device that the implantable medical lead has adequate integrity by having impedance measurements within an acceptable range.

10. The method of claim 9, wherein when the verifying results in a conclusion that the implantable lead has at least one impedance measurement outside of the acceptable range, then storing by the external device an indication that the implantable medical lead lacks adequate integrity to be acceptable for an MRI scan.

11. The method of claim 1, further comprising presenting allowable MRI scan settings for the implantable medical system.

12. The method of claim 1, further comprising verifying by the external device that a route that the implantable medical lead takes within the patient is acceptable for an MRI scan.

13. The method of claim 1, further comprising verifying by the external device that a placement of the implantable medical device within the patient is acceptable for an MRI scan.

14. The method of claim 8, further comprising storing an indication of when the implantable medical device has entered the MRI safe state.

15. A method of checking whether a magnetic resonance (MRI) image scan can be performed for a patient who has an implantable medical system, the method comprising:
establishing by an external device a telemetry communication session with the implantable medical system;
verifying by the external device that the implantable medical device has entered an MRI safe state by communicating with the implantable medical device over the telemetry communication session;
providing by the external device an indication of whether the implantable medical system is acceptable for the MRI scan based on the verifying of the implantable medical device;
analyzing by the external device MRI scan settings of an MRI machine by the external device taking measurements within the MM machine during an MRI scan by the MRI machine; and
providing by the external device an indication of whether the implantable medical system is acceptable for the MRI scan based on the analyzing of the MRI scan settings.

16. The method of claim 15, further comprising sending by the external device a command for the implantable medical device to enter the MRI safe state.

17. The method of claim 15, further comprising verifying by the external device that the implantable medical lead has adequate integrity by lacking short circuits and open circuits and wherein providing by the external device an indication of whether the implantable medical system is acceptable for the MRI scan is further based on the verifying of the implantable medical lead.

18. The method of claim 17, wherein when the verifying results in a conclusion that the implantable lead has at least one short circuit or at least one open circuit, then storing by the external device an indication that the implantable medical lead lacks adequate integrity to be acceptable for an MRI scan.

19. The method of claim 15, further comprising presenting allowable MRI scan settings for the implantable medical system.

20. The method of claim 15, further comprising verifying by the external device that a route that the implantable medical lead takes within the patient is acceptable for an MRI scan and wherein providing by the external device an indication of whether the implantable medical system is acceptable for the MRI scan is further based on the verifying of the implantable medical lead.

21. The method of claim 15, further comprising verifying by the external device that a placement of the implantable medical device within the patient is acceptable for an MRI scan.

22. A method of checking whether a magnetic resonance (MRI) image scan can be performed for a patient who has an implantable medical system, the method comprising:
establishing by an external device a telemetry communication session with the implantable medical system;
verifying by the external device that the implantable medical lead has adequate integrity by lacking short circuits and open circuits by communicating with the implantable medical device over the telemetry communication session;
providing by the external device an indication of whether the implantable medical system is acceptable for the MRI scan based on the verifying of the implantable medical lead;
analyzing by the external device MRI scan settings of an MRI machine by the external device taking measurements within the MM machine during an MRI scan by the MRI machine; and
providing by the external device an indication of whether the implantable medical system is acceptable for the MRI scan based on the analyzing of the MRI scan settings.

23. The method of claim 22, further comprising sending by the external device a command for the implantable medical device to enter an MRI safe state.

24. The method of claim 22, wherein when the verifying results in a conclusion that the implantable lead has at least one short circuit or at least one open circuit, then storing by the external device an indication that the implantable medical lead lacks adequate integrity to be acceptable for an MRI scan.

25. The method of claim 22, further comprising presenting allowable MRI scan settings for the implantable medical system.

26. The method of claim 22, further comprising verifying by the external device that a route that the implantable medical lead takes within the patient is acceptable for an MRI scan.

27. The method of claim 22, further comprising verifying by the external device that a placement of the implantable medical device within the patient is acceptable for an MRI scan and wherein providing by the external device an indication of whether the implantable medical system is acceptable for the MRI scan is further based on the verifying of the implantable medical device.

28. A method of checking whether a magnetic resonance (MRI) image scan can be performed for a patient who has an implantable medical system, the method comprising:
   analyzing by the external device MRI scan settings of an MRI machine by the external device taking measurements within the MM machine during an MRI scan by the MRI machine; and
   providing by the external device an indication of whether the implantable medical system is acceptable for the MRI scan based on the analyzing of the MRI scan settings.

29. The method of claim 28, further comprising sending by the external device a command for the implantable medical device to enter an MRI safe state.

30. The method of claim 28, further comprising presenting allowable MRI scan settings for the implantable medical system.

31. The method of claim 28, further comprising verifying by the external device that a route that the implantable medical lead takes within the patient is acceptable for an MRI scan and wherein providing by the external device an indication of whether the implantable medical system is acceptable for the MRI scan is further based on the verifying of the implantable medical lead.

32. The method of claim 28, further comprising verifying by the external device that a placement of the implantable medical device within the patient is acceptable for an MRI scan and wherein providing by the external device an indication of whether the implantable medical system is acceptable for the MRI scan is further based on the verifying of the implantable medical device.

33. A method of checking whether a magnetic resonance (MRI) image scan can be performed for a patient who has an implantable medical system, the method comprising:
   establishing by an external device a telemetry communication session with the implantable medical system;
   verifying by the external device that a route that the implantable medical lead takes within the patient is acceptable for an MRI scan by communicating with the implantable medical device over the telemetry communication session;
   providing by the external device an indication of whether the implantable medical system is acceptable for the MRI scan based on the verifying of the implantable medical lead;
   analyzing by the external device MRI scan settings of an MRI machine by the external device taking measurements within the MM machine during an MRI scan by the MRI machine; and
   providing by the external device an indication of whether the implantable medical system is acceptable for the MRI scan based on the analyzing of the MRI scan settings.

34. The method of claim 33, further comprising sending by the external device a command for the implantable medical device to enter an MRI safe state.

35. The method of claim 33, further comprising verifying by the external device that a placement of the implantable medical device within the patient is acceptable for an MRI scan and wherein providing by the external device an indication of whether the implantable medical system is acceptable for the MRI scan is further based on the verifying of the implantable medical device.

36. A method of checking whether a magnetic resonance (MRI) image scan can be performed for a patient who has an implantable medical system, the method comprising:
   establishing by an external device a telemetry communication session with the implantable medical system;
   verifying by the external device that a placement of the implantable medical device within the patient is acceptable for an MRI scan by communicating with the implantable medical device over the telemetry communication session;
   providing by the external device an indication of whether the implantable medical system is acceptable for the MRI scan based on the verifying of the implantable medical device;
   analyzing by the external device MRI scan settings of an MRI machine by the external device taking measurements within the MM machine during an MRI scan by the MRI machine; and
   providing by the external device an indication of whether the implantable medical system is acceptable for the MRI scan based on the analyzing of the MRI scan settings.

37. The method of claim 36, further comprising sending by the external device a command for the implantable medical device to enter an MRI safe state.

38. An external device for checking whether a magnetic resonance (MRI) image scan can be performed for a patient who has an implantable medical system, comprising:
   a processor configured to:
      establish a telemetry communication session with the implantable medical system;
      verify that an implantable medical device of the implantable medical system is of a type that is acceptable for the MRI scan by sending a query to the implantable medical system via the telemetry communication session;
      verify that an implantable medical lead of the implantable medical system is of a type that is acceptable for the MRI scan;
      provide an indication of whether the implantable medical system is acceptable for the MRI scan based on the verifying of the implantable medical device and the implantable medical lead;
      analyze MRI scan settings of an MRI machine by the processor taking measurements from within the MRI machine during an MRI scan by the MRI machine; and
      provide an indication of whether the implantable medical system is acceptable for the MRI scan based on the analyzing of the MRI scan settings.

39. An external device for checking whether a magnetic resonance (MRI) image scan can be performed for a patient who has an implantable medical system, comprising:

a processor configured to:
establish a telemetry communication session with the implantable medical system;
verify that the implantable medical device has entered an MRI safe state by communicating with the implantable medical device over the telemetry communication session;
provide an indication of whether the implantable medical system is acceptable for the MRI scan based on the verifying of the implantable medical device;
analyze MRI scan settings of an MRI machine by the processor taking measurements from within the MRI machine during an MRI scan by the MRI machine; and
provide an indication of whether the implantable medical system is acceptable for the MRI scan based on the analyzing of the MRI scan settings.

40. An external device for checking whether a magnetic resonance (MRI) image scan can be performed for a patient who has an implantable medical system, comprising:
a processor configured to:
establish a telemetry communication session with the implantable medical system;
verify by the external device that the implantable medical lead has adequate integrity by lacking short circuits and open circuits by communicating with the implantable medical device over the telemetry communication session;
provide an indication of whether the implantable medical system is acceptable for the MRI scan based on the verifying of the implantable medical lead;
analyze MRI scan settings of an MRI machine by the processor taking measurements from within the MRI machine during an MRI scan by the MRI machine; and
provide an indication of whether the implantable medical system is acceptable for the MRI scan based on the analyzing of the MRI scan settings.

41. An external device for checking whether a magnetic resonance (MRI) image scan can be performed for a patient who has an implantable medical system, comprising:
a processor configured to:
analyze MRI scan settings of an MRI machine by the processor taking measurements from within the MRI machine during an MRI scan by the MRI machine; and
provide an indication of whether the implantable medical system is acceptable for the MRI scan based on the analyzing of the MRI scan settings.

42. An external device for checking whether a magnetic resonance (MRI) image scan can be performed for a patient who has an implantable medical system, comprising:
a processor configured to:
establish a telemetry communication session with the implantable medical system;
verify that a route that the implantable medical lead takes within the patient is acceptable for an MRI scan by communicating with the implantable medical system over the telemetry communication session;
provide an indication of whether the implantable medical system is acceptable for the MRI scan based on the verifying of the implantable medical lead;
analyze MRI scan settings of an MRI machine by the processor taking measurements from within the MRI machine during an MRI scan by the MRI machine; and
provide an indication of whether the implantable medical system is acceptable for the MRI scan based on the analyzing of the MRI scan settings.

43. An external device for checking whether a magnetic resonance (MRI) image scan can be performed for a patient who has an implantable medical system, comprising:
a processor configured to:
establish a telemetry communication session with the implantable medical system;
verify that a placement of the implantable medical device within the patient is acceptable for an MRI scan by communicating with the implantable medical device over the telemetry communication session;
provide an indication of whether the implantable medical system is acceptable for the MRI scan based on the verifying of the implantable medical device;
analyze MRI scan settings of an MRI machine by the processor taking measurements from within the MRI machine during an MRI scan by the MRI machine; and
provide an indication of whether the implantable medical system is acceptable for the MRI scan based on the analyzing of the MRI scan settings.

\* \* \* \* \*